(12) United States Patent
Turton

(10) Patent No.: US 8,188,324 B2
(45) Date of Patent: May 29, 2012

(54) PREPARATION OF $^{11}$C METHYL IODIDE

(75) Inventor: David Robert Turton, London (GB)

(73) Assignee: Hammersmith Imanet Limited, London (GB)

( * ) Notice: Subject to any disclaimer, the term of this patent is extended or adjusted under 35 U.S.C. 154(b) by 795 days.

(21) Appl. No.: 11/909,469

(22) PCT Filed: Mar. 23, 2006

(86) PCT No.: PCT/GB2006/001053
§ 371 (c)(1),
(2), (4) Date: Sep. 24, 2007

(87) PCT Pub. No.: WO2006/100481
PCT Pub. Date: Sep. 28, 2006

(65) Prior Publication Data
US 2008/0207909 A1      Aug. 28, 2008

(30) Foreign Application Priority Data
Mar. 23, 2005    (GB) .................... 0505952.2

(51) Int. Cl.
*C07C 17/00* (2006.01)
*C07D 239/72* (2006.01)
*C07D 307/02* (2006.01)

(52) U.S. Cl. ......... 570/240; 570/181; 544/283; 549/472

(58) Field of Classification Search ............... 546/284.7; 570/181, 240; 423/256; 544/283; 549/472
See application file for complete search history.

(56) References Cited

U.S. PATENT DOCUMENTS
2002/0155063 A1    10/2002    Wilson et al.

FOREIGN PATENT DOCUMENTS
| | | |
|---|---|---|
| EP | 0462546 | 9/2001 |
| JP | 2000086632 | 3/2000 |
| JP | 2005053803 | 3/2005 |

OTHER PUBLICATIONS
GB0505952.2 Search Report Jul. 1, 2005.
PCT/GB2006/001053 Int'l Search Report and Written Opinion dated Nov. 14, 2006.
Sarkadi, E., et.al. "Synthesis of [11C]methanol on alumina column for production of [11C]methyl iodide" Radiochimica Acta vol. 83, 1998 pp. 49-52.
Crouzel, C. et.al. "Recommendations for a practical production of [11C]methyl iodide" Appl. Radiat. Isot., vol. 38, nl. 8, 1987, pp. 601-603.
Davenport, R.J., et.al. "Radiosynthesis of [11C]GB67—a potential radioligand for the study of alpha-1-adrenoreceptros with PET" J. Label. Comp. Radiopharm., vol. 37, 1995, pp. 387-388.
Law, M.P., et.al. "Evaluation of [11C]GB67, a novel radioligand for imging myocardial alpha-1-adrenoreceptors with positron emission tomography" European Journal of Nuclear Medicine, vol. 27, No. 1, 2000, pp. 7-17.

*Primary Examiner* — Taylor Victor Oh

(57) ABSTRACT

A process for the preparation of $^{11}$C methyl iodide comprises coating the internal surface of a first reaction vessel with a solution of lithium aluminum hydride, wherein the first reaction vessel has an internal diameter not greater than about 1.5 mm; introducing $^{11}$C carbon dioxide into the first reaction vessel such that it is reduced by the lithium aluminum hydride to give a reduction product; and reacting the reduction product with hydriodic acid.

17 Claims, 1 Drawing Sheet

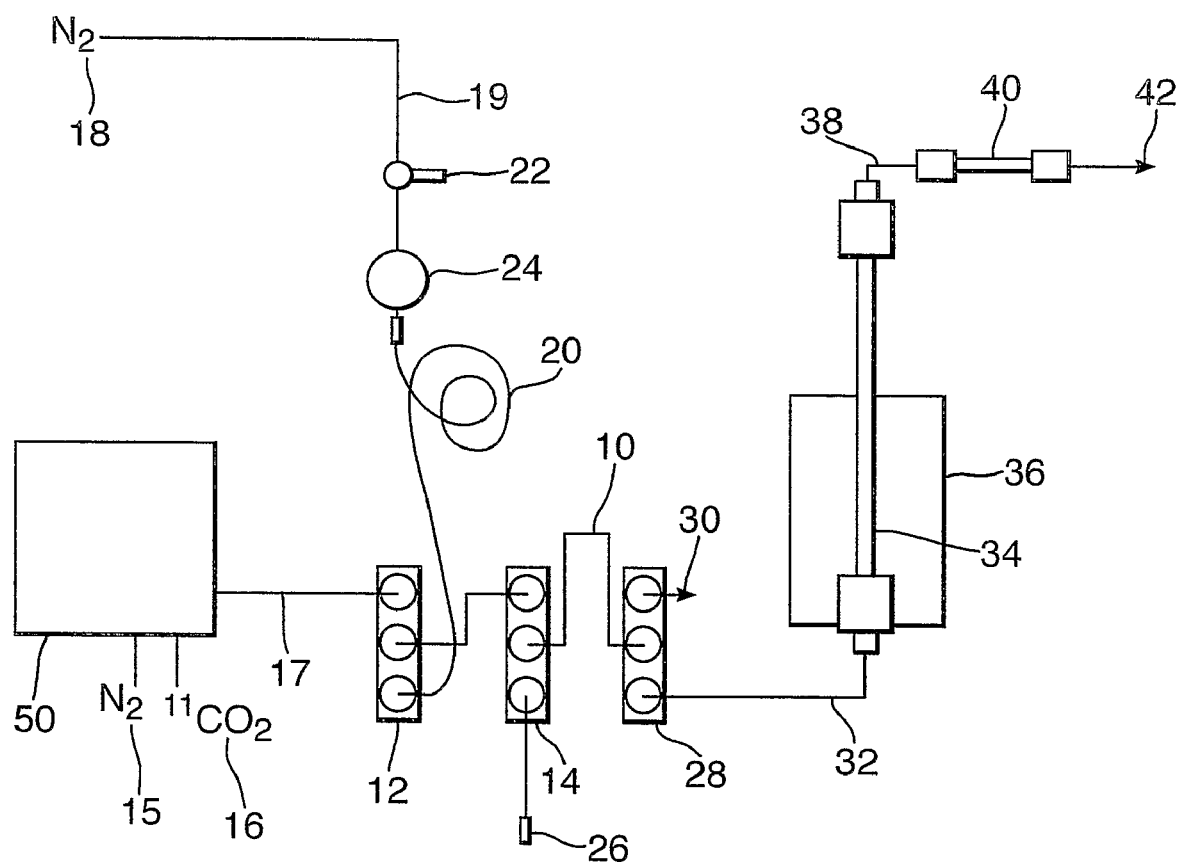

PREPARATION OF $^{11}$C METHYL IODIDE

This application is a filing under 35 U.S.C. 371 of international application number PCT/GB2006/001053, filed Mar. 23, 2006, which claims priority to application number 0505952.2 filed Mar. 23, 2005, in Great Britain the entire disclosure of which is hereby incorporated by reference.

The present invention relates to a process for the preparation of $^{11}$C methyl iodide and to apparatus for carrying out this process. In particular, the invention relates to a process comprising the reduction of $^{11}CO_2$ followed by the reaction of the product with hydriodic acid. The process yields a product with a much higher specific activity than conventional processes.

Tracer compounds used in positron emission tomography (PET) are labelled with a variety of positron emitting isotopes, for example $^{11}$C. However, one problem with the use of $^{11}$C as a label is that it has a half-life of only 20.4 minutes. This means that, in order to obtain a tracer compound with a sufficiently high specific activity to be useful in PET, it is necessary to synthesise the compound as rapidly as possible.

$^{11}$C-labelled PET tracer compounds are often synthesised by reacting a precursor (for example an amine) with $^{11}$C methyl iodide and the present invention relates to a process for producing $^{11}$C methyl iodide. In order to produce a tracer, having high specific activity, it is important that the intermediate $^{11}$C methyl iodide itself has high specific activity and, consequently, that it is produced using a reaction process which is as rapid as possible.

This is well known to those of skill in the art and a number of authors have attempted to address the problems of producing $^{11}$C methyl iodide having high specific activity. For example Larsen et al (WO 96/15086) teach the production of $^{11}$C methyl iodide by halogenation of $^{11}$C methane in a gas phase process and DE-A-4420670 relates to the production of $^{11}$C methyl iodide from $^{11}$C carbon monoxide or carbon dioxide in a gas phase process.

An alternative process for the production of $^{11}$C methyl iodide is taught in EP-A-0462546. In this process, $^{11}CO_2$ is bubbled through a solution of a reducing agent such as lithium aluminium hydride ($LiAlH_4$). The reducing agent solution is evaporated by heating and then hydriodic acid is added to the residue. The authors recognised that it was important to produce a product of high specific activity and introduced a number of control devices into their apparatus.

The present invention relates to a process for the production of $^{11}$C methyl iodide which yields a product having a higher specific activity than conventional processes and yet is simpler than processes described in the prior art. In particular, the quantity of $LiAlH_4$ in the process of the present invention is much lower than in conventional processes. $LiAlH_4$ often contains small amounts of methanol/methoxide which is a reduction product of atmospheric $CO_2$ which has come into contact with the $LiAlH_4$. Therefore, reducing the amount of $LiAlH_4$ leads to a reduction in the amount of stable methanol/methoxide contaminating the $^{11}$C methanol/methoxide intermediate. In addition, the reaction using the process of the present invention proceeds much more rapidly than conventional reactions and this leads to a product which has a higher specific activity.

In a first aspect of the present invention, there is provided a process for the production of $^{11}$C methyl iodide, the process comprising:

a) coating the internal surface of a first reaction vessel with a solution of lithium aluminium hydride, wherein the first reaction vessel has an internal diameter not greater than about 1.5 mm;

b) introducing $^{11}$C carbon dioxide into the first reaction vessel such that it is reduced by the lithium aluminium hydride to give a reduction product;

c) providing a second reaction vessel in fluid communication with the first reaction vessel, said second reaction vessel being heated; and, d) passing hydriodic acid through the first reaction vessel, which contains the reduction product, into the second reaction vessel where $^{11}$C methyl iodide is produced.

Heating the second reaction vessel ensures that the hydriodic acid evaporates and that the iodination reaction proceeds rapidly. Typically, the second reaction vessel is heated to a temperature of about 150 to 200° C., preferably 160 to 190° C.

$^{11}CO_2$ is introduced into the first reaction vessel at a flow rate of about 8 ml/min. The gas flow rate for the addition of hydriodic acid and hence the gas flow to distil the methyl iodide is about 15 ml/min.

The inventors have discovered that the use of a reaction vessel having a small internal diameter for the first part of the process leads to a product which has a much higher specific activity than conventionally produced $^{11}$C methyl iodide. One reason for this is that the quantity of $LiAlH_4$ is much lower than in conventional processes. As explained above, $LiAlH_4$ is often contains small amounts of methanol/methoxide and therefore reducing the amount of $LiAlH_4$ leads to a reduction in the amount of stable methanol/methoxide contaminating the $^{11}$C methanol/methoxide intermediate. In addition, the reaction using the process of the present invention proceeds much more rapidly than conventional reactions and this leads to a product which has a higher specific activity.

Radiochemical processes which make use of narrow bore reaction vessels are known. For example, US 2002/0155063 relates to a process in which $^{11}$C methyl iodide and a PET precursor compound are reacted together in an HPLC injection loop. However, no prior author appears to have recognised the benefits of carrying out the reduction of $^{11}CO_2$ in such a vessel.

The first reaction vessel preferably takes the form of a tube with a narrow bore, for example an HPLC loop. The internal diameter of the reaction vessel is usually in the range of about 1 micrometre to 1.5 mm, preferably 40 to 200 μm. It is particularly convenient if the first reaction vessel is open at both ends so that the reagents can be flushed through.

The length of the first reaction vessel will be chosen such that it is long enough for the $^{11}CO_2$ to react fully with the $LiAlH_4$ but is sufficiently short for the reaction time to be minimised. A convenient length for the first reaction vessel is from about 5 cm to 50 cm long, more usually 5 cm to 20 cm and typically about 15 cm.

The $LiAlH_4$ solution may be introduced into the first reaction vessel by any convenient means, for example by injection. Because of the narrow bore of the first reaction vessel, the $LiAlH_4$ solution forms a coating on the internal walls of the first reaction vessel.

Suitable solvents for $LiAlH_4$ are well known to those of skill in the art and an example of such a solvent is tetrahydrofuran (THF). The $LiAlH_4$ solution will generally have a concentration of about 0.05 to 1M, more usually 0.05M to 0.5M and typically about 0.1M.

In order to minimise the amount of atmospheric $CO_2$ in the first reaction vessel, it is preferable to flush out the first reaction vessel with an inert gas such as nitrogen or argon before coating the internal surface with the $LiAlH_4$ solution.

After the LiAlH$_4$ solution has been introduced into the first reaction vessel, it is advantageous to blow an inert gas such as nitrogen through the first reaction vessel to remove excess reagent.

The $^{11}CO_2$ used in step (b) may be produced by any conventional means, for example it may be produced on a cyclotron and then cryogenically trapped. It may be introduced into the first reaction vessel by any convenient method, for example in a stream of an inert gas such as nitrogen or argon.

The hydriodic acid is present as an aqueous solution containing from 40 to 60% hydrogen iodide, and preferably from 50 to 60% hydrogen iodide. Suitable hydriodic acid solutions are commercially available.

The hydrogen iodide may be introduced into the first reaction vessel in a stream of an inert gas, for example nitrogen or argon, but preferably nitrogen.

It is particularly preferred that the second reaction vessel is positioned in a generally vertical orientation and that only the lower portion is heated. This configuration allows for the iodination reaction to take place in the lower part of the reaction vessel and for unreacted hydriodic acid and reduction product to condense in the upper part of the reaction vessel and fall back to the lower part.

After the iodination reaction, the $^{11}C$ methyl iodide product may be passed over a drying agent to remove water vapour. It is particularly useful to use a drying agent such as solid sodium hydroxide since this will also remove any unreacted hydriodic acid from the $^{11}C$ methyl iodide product.

As mentioned above, $^{11}C$ methyl iodide is a useful precursor for the production of $^{11}C$-labelled PET tracer compounds and therefore the process of the invention may comprise an additional step of reacting the $^{11}C$ methyl iodide with a non-radiolabelled precursor of a $^{11}C$-labelled PET tracer compound to produce a $^{11}C$-labelled PET tracer compound.

The precursor compound may be an amine, amide, hydroxide, sulfide, sulfonamide or any other compound which can be methylated by reaction with methyl iodide.

One PET tracer compound which can be produced by the process of the present invention is N-[6[(4-amino-6,7-dimethoxy-2-quinazolinyl)methylamino]hexyl]-2-furancarboxy-[$^{11}C$]-methylamide. This compound may be produced by reacting the precursor compound, N-[6[(4-amino-6,7-dimethoxy-2-quinazolinyl)methylamino]hexyl]-2-furancarboxamide with $^{11}C$ methyl iodide in the presence of a strong base such as sodium hydride.

Therefore, in a further aspect of the invention, there is provided a process for the preparation of N-[6[(4-amino-6,7-dimethoxy-2-quinazolinyl)methylamino]hexyl]-2-furancarboxy-[$^{11}C$]-methylamide, the process comprising the steps of:

a) coating the internal surface of a first reaction vessel with a solution of lithium aluminium hydride, wherein the first reaction vessel has an internal diameter not greater than about 1.5 mm;
b) introducing $^{11}C$ carbon dioxide into the first reaction vessel such that it is reduced by the lithium aluminium hydride to give a reduction product;
c) producing a second reaction vessel in fluid communication with the first reaction vessel, said second reaction vessel being heated;
d) passing hydroiodic acid through the first reaction vessel, which contains the reduction product, into the second reaction vessel where $^{11}C$ methyl iodide is produced; and,
e) reacting the $^{11}C$ methyl iodide with N-[6[(4-amino-6,7-dimethoxy-2-quinazolinyl)methylamino]hexyl]-2-furancarboxamide under basic conditions to yield N-[6[(4-amino-6,7-dimethoxy-2-quinazolinyl)methylamino]hexyl]-2-furancarboxy-[$^{11}C$]-methylamide.

Preferred features of steps (a) to (d) are as detailed for the first aspect of the invention.

It has been found that particularly successful results are obtained when step (e) of the process are carried out in a third reaction vessel which is similar to the first reaction vessel. Therefore, the third reaction vessel preferably has an internal diameter not greater than about 1.5 mm and preferably takes the form of a tube with a narrow bore, for example an HPLC loop. The internal diameter of the third reaction vessel is usually in the range of about 1 micrometre to 1.5 mm, preferably 40 to 200 µm. It is particularly convenient if the first reaction vessel is open at both ends so that the reagents can be flushed through.

The length of the third reaction vessel will be chosen such that it is long enough for the $^{11}C$ methyl iodide to react fully with the N-[6[(4-amino-6,7-dimethoxy-2-quinazolinyl)methylamino]hexyl]-2-furancarboxamide but is sufficiently short for the reaction time to be minimised. A convenient length for the first reaction vessel is from about 5 cm to 50 cm long, more usually 5 cm to 20 cm and typically about 10 cm.

In step (e) it is preferred that the internal surface of the third reaction vessel is coated with a solution of N-[6[(4-amino-6,7-dimethoxy-2-quinazolinyl)methylamino]hexyl]-2-furancarboxamide and that a solution of $^{11}C$ methyl iodide is passed though the vessel.

The invention also relates to apparatus for carrying out the method. Therefore, in a further aspect there is provided apparatus for the production of $^{11}C$ methyl iodide, the apparatus comprising:

a first reaction vessel having an internal diameter not greater than about 1.5 mm;
a second reaction vessel connected to the first reaction vessel, via a valve which has a first and a second position such that when the valve is in the first position, the first and second reaction vessels are not in fluid communication and when the valve is in the second position the first and second reaction vessels are in fluid communication such that a mixture of hydriodic acid and a reduction product from the first reaction vessel can pass from the first reaction vessel into the second reaction vessel; and
means for heating the second reaction vessel.

It is greatly preferred that when the valve is in the position, the first reaction vessel is connected to a waste line. The waste is gas used to flush out the first reaction vessel and excess LiAlH$_4$.

Optionally, the apparatus may also comprise one or more of:

means for flushing out the first reaction vessel with nitrogen;
means for introducing a solution of LiAlH$_4$ into the first reaction vessel such that the solution of LiAlH$_4$ forms a coating on the internal surface of the first reaction vessel;
means for introducing $^{11}CO_2$ into the first reaction vessel;
means for passing hydriodic acid into the first reaction vessel; and
means for removing excess hydrogen iodide and water from the product.

The means for flushing out the first reaction vessel with nitrogen may comprise a connection to a nitrogen source.

The means for introducing a solution of LiAlH$_4$ into the first reaction vessel may comprise an injection system.

The means for introducing $^{11}CO_2$ into the first reaction vessel may comprise a cryogenic trap containing the $^{11}CO_2$, a nitrogen source, means for mixing the $^{11}CO_2$ from the trap with the nitrogen source and a first inlet tube which carries the mixture of nitrogen and $^{11}CO_2$ to the first reaction vessel.

Optionally, the nitrogen used to carry the $^{11}CO_2$ and the nitrogen used for flushing out the first reaction vessel may be taken from the same source.

The means for passing hydriodic acid through the first reaction vessel into the second reaction vessel may comprise a hydriodic acid loop, a stream of nitrogen flowing through the hydriodic acid loop and means for introducing hydriodic acid into the nitrogen stream.

The nitrogen stream carrying the hydriodic acid may enter the first reaction vessel via an inlet valve. The hydriodic acid may be an aqueous solution of hydrogen iodide as described above for the first aspect of the invention.

The apparatus may also comprise a waste line connected to the valve between the first and second reaction vessels through which gas or by-products of the reaction can be vented.

The second reaction vessel may comprise a tube having an inlet end and an outlet end. The tube typically has an internal diameter of about 0.2-20 mm, more usually about 0.5 to 10 mm and may be constructed from a heat conducting material, particularly a metal such as stainless steel.

The means for heating the second reaction vessel may comprise a block heater surrounding the reaction vessel. Typically, the heating means is capable of heating the second reaction vessel to a temperature of from about 150 to 200° C., preferably 160 to 190° C.

It is greatly preferred that the second reaction vessel is in a generally vertical orientation such that the inlet end is lower than its outlet end and that only the lower (inlet) end of the second reaction vessel is heated. This arrangement allows the aqueous mixture of reduction product, hydriodic acid and water to evaporate in the lower portion of the tube and the gaseous reagents to react to form the $^{11}C$ methyl iodide. When the mixture reaches the upper unheated part of the reaction vessel the unreacted hydriodic acid and reduction product will recondense and fall to the bottom of the tube, while the more volatile $^{11}C$ methyl iodide passes to the outlet of the second reaction vessel.

The invention will now be described in greater detail, by way of example only with reference to the figures and examples.

FIG. 1 is a schematic representation of apparatus for preparing $^{11}C$ methyl iodide.

The apparatus shown in FIG. 1 comprises a reaction vessel (10), which is an HPLC grade stainless steel tube having an external diameter of 1/16 inches (1.58 mm) and 10 cm in length. First and second three port input valves (12) and (14) are connected to the input side of the reaction vessel (10). A first source of nitrogen (15) and source of $^{11}CO_2$ (16) are both connected to the first input valve (12) via a cryogenic trap (50) and a line (17). The cryogenic trap (50) is known from the prior art and can be set either so that the trap is cooled, trapping $^{11}CO_2$ and allowing nitrogen to pass through the line (17) or so that the trap is not cooled and a mixture of $^{11}CO_2$ and nitrogen passes through the line (17). A second source of nitrogen (18) is also connected to the first input valve (12) via a nitrogen line (19) and a hydriodic acid loop (20), which is an HPLC loop formed from a material such as polytetrafluoroethylene (PTFE). The nitrogen line (19) has a needle valve (22), which controls the flow rate of the nitrogen. Between the nitrogen line (19) and the hydriodic acid loop (20) is a valve (24) through which hydriodic acid can be introduced into the hydriodic acid loop (20).

Connected to the second input valve (14) is an injection system (26) through which LiAlH$_4$ can be introduced into the reaction vessel (10) via the second input valve (14).

A three port output valve (28) is connected to the output side of the reaction vessel (10). One port of the output valve (28) is connected to a waste line (30) and another to a second reaction vessel (34) via a first output line (32). The second reaction vessel comprises a stainless steel tube having an external diameter of ¼ inches (6.35 mm).

The second reaction vessel is held in a vertical orientation and its lower end is surrounded by an aluminium block heater (36) which heats the temperature of the second reaction vessel (34) to a temperature of 185° C. The output end of the second reaction vessel (34) is connected to a sodium hydroxide trap (40) via a second output line (38). The sodium hydroxide trap (40) comprises a tube packed with solid sodium hydroxide which removes excess water and hydrogen iodide from the product and is connected to a third output line (42). The trap (40) may be made from any suitable material, for example glass.

In use, the cryogenic trap (50) is set in the uncooled configuration such that nitrogen passes from the nitrogen source (15) and through the line (17) to flush out the first reaction vessel (10) in order to remove atmospheric carbon dioxide from the first reaction vessel (10). The nitrogen passes through the first reaction vessel (10) and to the waste line (30) via the output valve (28). A 0.1M solution of LiAlH$_4$ in tetrahydrofuran (THF) is injected into the first reaction vessel (10) via the injection system (26) and the second input valve (14). The first reaction vessel (10) is then flushed again with nitrogen as before in order to remove excess LiAlH$_4$ solution from the first reaction vessel (10).

The cryogenic trap (50) is then reconfigured so that it is in the cooled position: $^{11}CO_2$ from the cyclotron is then trapped in the cryogenic trap.

The cryogenic trap (50) is then reconfigured so that it is in the uncooled position such that $^{11}CO_2$ from is introduced into the first line (17) and thus passes into the first reaction vessel (10) via the first and second input valves (12) and (14). In the first reaction vessel, the $^{11}CO_2$ is reduced to $^{11}C$ methoxide.

Next, hydriodic acid (a 57% aqueous solution of hydrogen iodide) is introduced into the hydriodic acid loop (20) via the valve (24). The hydriodic acid loop (20) has previously been flushed with nitrogen from the second nitrogen source (18). Nitrogen from the second nitrogen source (18) carries the hydriodic acid to the first and second input valves (12) and (14), and into the first reaction vessel (10) where it flushes the $^{11}C$ methoxide product into the output valve (30), along the first product line (32) and into the second reaction vessel (34).

The second reaction vessel (34) is pre-heated to 185° C. or maintained at 185° C. from the start of the process by the aluminium block heater (36) and this ensures that the aqueous solution containing the hydrogen iodide and the $^{11}C$ methoxide evaporates and that the reaction between the two reagents proceeds rapidly. When the reagents reach the upper, unheated part of the second reaction vessel (34), unreacted hydrogen iodide and reduction product condense and fall back to the lower part of the tube, while the more volatile $^{11}C$ methyl iodide product leaves the second reaction vessel (34) via the second product line (38).

The $^{11}C$ methyl iodide product passes from the second output line (38) to a trap (40) which contains solid sodium hydroxide. This removes both unreacted hydrogen iodide and excess water from the product.

After passing through the trap (40), the $^{11}C$ methyl iodide produced in the apparatus passes via a third output line (42) to a reaction vessel (not shown) in which the $^{11}C$ methylation of a PET precursor compound takes place.

EXAMPLE 1

Preparation of N-[6[(4-amino-6,7-dimethoxy-2-quinazolinyl)methylamino]hexyl]-2-furancarboxy-[$^{11}$C]-methylamide This example demonstrates that preparation of N-[6[(4-amino-6,7-dimethoxy-2-quinazolinyl)methylamino]hexyl]-2-furancarboxy-[$^{11}$C]-methylamide from $^{11}$C methyl iodide produced according to the method of the invention has a higher specific activity than the same product prepared using $^{11}$C methyl iodide produced in conventional apparatus in which the LiAlH$_4$ and the $^{11}$CO$_2$ are reacted in a conventional reaction vessel rather than in a small bore tube such as an HPLC loop.

$^{11}$C methyl iodide was prepared in the apparatus shown in FIG. 1 according to the method described above. Thus, 200 μL of a 0.1M solution of LiAlH$_4$ in THF was introduced into the first reaction vessel (the loop, 10), following which, the loop (10) was flushed through with nitrogen. $^{11}$CO$_2$ was then passed through the loop where it was trapped and converted to $^{11}$C methoxide.

Next, hydriodic acid was introduced into the loop via the hydriodic acid loop (20) (100 μL of a 57% aqueous solution of hydrogen iodide) such that the $^{11}$C methoxide product was carried with the hydriodic acid into the second reaction vessel (34).

The hydrogen iodide reacts with the methoxide to give the product, $^{11}$C methyl iodide, which is purified by passing through the sodium hydroxide trap (40).

The $^{11}$C methyl iodide produced was fed directly into a second loop which had previously been flushed with nitrogen and of which the internal surface was coated with the precursor compound N-[6[(4-amino-6,7-dimethoxy-2-quinazolinyl)methylamino]hexyl]-2-furancarboxamide (0.3-0.5 mg in 100 μL dimethyl formamide). The reaction was conducted in the presence of 0.7-1.3 mg sodium hydride.

The yield of the product on three synthetic runs and the specific activity of the product at the end of the synthesis are shown in Table 1.

| Amount of product μg | Radioactivity at end of synthesis (mCi) | Specific activity at end of synthesis (MBq/μmol) | Radiochemical purity (%) |
| --- | --- | --- | --- |
| 3.1 | 115.9 | 610,145 | 100 |
| 2.0 | 136.9 | 1,116,899 | 100 |
| 1.5 | 115.7 | 1,258,585 | 100 |

In comparison, the same product prepared using conventionally prepared $^{11}$C methyl iodide usually has a specific activity of about 50,000 to 100,000 MBq/μmol. It can therefore be seen that the present invention provides $^{11}$C methyl iodide with much greater specific activity which can, in turn, be converted to a product having higher specific activity.

What is claimed is:

1. A process for the production of $^{11}$C methyl iodide, the process comprising:
   a) coating the internal surface of a first reaction vessel with a solution of lithium aluminium hydride by (i) introducing said solution into a first reaction vessel and then (ii) blowing an inert gas through the first reaction vessel to remove excess lithium aluminium hydride, wherein the first reaction vessel has an internal diameter not greater than about 1.5 mm;
   b) introducing $^{11}$C carbon dioxide into the first reaction vessel such that it is reduced by the lithium aluminium hydride to give a reduction product;
   c) providing a second reaction vessel in fluid communication with the first reaction vessel, said second reaction vessel being heated; and,
   d) passing hydriodic acid through the first reaction vessel, which contains the reduction product, into the second reaction vessel where $^{11}$C methyl iodide is produced.

2. A process as claimed in claim 1 wherein the first reaction vessel is a tube with an internal diameter of about 1 micrometre to 1.5 mm.

3. A process as claimed in claim 2 wherein the first reaction vessel is a tube with an internal diameter of about 40 to 200 μm.

4. A process as claimed in claim 1, wherein the first reaction vessel is open at both ends.

5. A process as claimed in claim 1, wherein the first reaction vessel is from about 5 cm to 50 cm long.

6. A process as claimed in claim 5, wherein the first reaction vessel is from about 5 cm to 20 cm long.

7. A process as claimed in claim 1, wherein the LiAlH$_4$ solution is introduced into the first reaction vessel by injection.

8. A process as claimed in claim 1, wherein the LiAlH$_4$ solution comprises a 0.05 to 1M solution of LiAlH$_4$ in tetrahydrofuran.

9. A process as claimed in claim 1, further comprising the step of flushing out the first reaction vessel with an inert gas before coating the internal surface with the LiAlH$_4$ solution.

10. A process as claimed in claim 1 wherein the $^{11}$CO$_2$ is introduced into the first reaction vessel by in a stream of an inert gas.

11. A process as claimed in claim 1 wherein the hydriodic acid is present as an aqueous solution containing from 40 to 60% hydrogen iodide.

12. A process as claimed in claim 1 wherein the hydrogen iodide is introduced into the first reaction vessel in a stream of an inert gas.

13. A process as claimed in claim 1, wherein the second reaction vessel is heated to a temperature of about 150 to 200° C.

14. A process as claimed in claim 1, wherein the second reaction vessel is in a vertical orientation such that its inlet end is lower than its outlet end, and that only the inlet end of said second reaction vessel is heated.

15. A process as claimed in claim 1, further comprising the additional step of reacting the $^{11}$C methyl iodide with a non-radiolabelled precursor of a $^{11}$C-labelled PET tracer compound to produce a $^{11}$C-labelled PET tracer compound.

16. A process as claimed in claim 15, wherein the precursor compound is an amine, amide, hydroxide, sulfide, sulfonamide or any other compound which can be methylated by reaction with methyl iodide.

17. A process as claimed in claim 15, wherein the precursor compound is N-[6-[(4-amino-6,7-dimethoxy-2-quinazolinyl)methylamino]hexyl]-2-furancarboxamide.

* * * * *